United States Patent [19]

Bickel et al.

[11] 4,067,979
[45] Jan. 10, 1978

[54] CEPHALOSPORINS HAVING AN α-ACYLOXYACETIC ACID SIDE CHAIN

[75] Inventors: Hans Bickel, Binningen; Karoly Kocsis, Basel; Heinrich Peter, Binningen, all of Switzerland

[73] Assignee: Ciba-Geigy Corporation, Ardsley, N.Y.

[21] Appl. No.: 565,327

[22] Filed: Apr. 7, 1975

[30] Foreign Application Priority Data

Apr. 11, 1974 Switzerland .................. 5179/74

[51] Int. Cl.$^2$ ............... A61K 31/545; C07D 501/36
[52] U.S. Cl. ........................ 424/246; 260/250 A; 260/287 H; 260/295 R; 260/308 R; 544/27
[58] Field of Search ................................ 260/243 C

[56] References Cited

U.S. PATENT DOCUMENTS

| | | | |
|---|---|---|---|
| 3,812,116 | 5/1974 | Takano et al. | 260/243 C |
| 4,000,133 | 12/1976 | Kariyone et al. | 260/243 C |
| 4,006,138 | 2/1977 | Yang | 260/243 C |

Primary Examiner—Nicholas S. Rizzo
Assistant Examiner—David E. Wheeler
Attorney, Agent, or Firm—John J. Maitner

[57] ABSTRACT

The invention relates to compounds of the formula

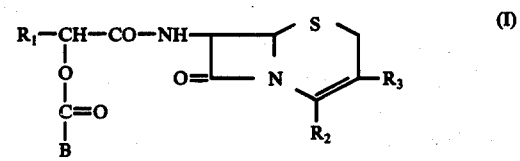

wherein $R_1$ denotes optionally substituted phenyl, thienyl, furyl or 1,4-cyclohexadienyl, $R_2$ represents a free carboxyl group or an esterified carboxyl group which can be split physiologically, $R_3$ represents hydrogen, lower alkoxy or an optionally substituted methyl group, and B represents a monosubstituted or polysubstituted six-membered ring with 1 to 3 ring nitrogen atoms which is bonded to the carbonyl group —C(=O)— by one of its ring carbon atoms, and the salts of such compounds which have salt-forming groups, which compounds possess antibiotic properties.

7 Claims, No Drawings

CEPHALOSPORINS HAVING AN α-ACYLOXYACETIC ACID SIDE CHAIN

The invention relates to new therapeutically valuable derivatives of 7-amino-ceph-3-em-4-carboxylic acid and their salts, processes for their manufacture and pharmaceutical preparations which contain the new compounds.

In particular, the invention relates to compounds of the formula

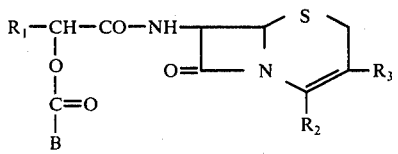

wherein $R_1$ denotes optionally substituted phenyl, thienyl, furyl or 1,4-cyclohexadienyl, $R_2$ represents a free carboxyl group or an esterified carboxyl group which can be split physiologically, $R_3$ represents hydrogen, lower alkoxy or an optionally substituted methyl group and B represents a monosubstituted or polysubstituted six-membered ring with 1 to 3 ring nitrogen atoms which is bonded to the carbonyl group —C(=O)— by one of its ring carbon atoms, and the salts of such compounds which have a salt-forming group, including the inner salts.

Unless defined otherwise, the general expressions employed in the preceding and following text have the following meanings:

Lower alkyl is a straight-chain or branched alkyl group with 1 to 7, preferably with up to 4, carbon atoms, and denotes, for example, methyl, ethyl, propyl, isopropyl, butyl, isobutyl, tert.-butyl, pentyl, hexyl or heptyl.

Correspondingly, lower alkoxy is methoxy, ethoxy, propoxy, isopropoxy, butoxy, isobutoxy, tert.-butoxy, pentyloxy, hexyloxy or heptyloxy and lower alkylmercapto is methylmercapto, ethylmercapto, propylmercapto, isopropylmercapto, butylmercapto, isobutylmercapto, tert.-butylmercapto, pentylmercapto hexylmercapto or heptylmercapto.

Lower alkanoyl is a straight-chain or branched lower alkylcarbonyl group with 1 to 8, preferably up to 5, carbon atoms, and denotes, for example, formyl, acetyl, propionyl, butyryl, valeryl, isovaleryl or heptanecarbonyl.

Halogen is, in particular, fluorine, chlorine or bromine.

Aryl is a monocyclic or polycyclic, such as bicyclic or tricyclic, aromatic radical with up to 14 carbon atoms and is, for example, phenyl, naphthyl or anthranyl, which can optionally be substituted, for example by hydroxyl, lower alkoxy, lower alkyl, halogen or nitro.

Examples of substituents of the cyclic radicals $R_1$ are hydroxyl, lower alkyl, such as methyl, lower alkoxy, such as methoxy, halogen atoms, such as fluorine or chlorine, halogeno-lower alkyl, such as trifluoromethyl, nitro, carbamoyl and acyl, especially lower alkanoyl, such as acetyl, or optionally protected amino.

The substituent $R_2$ is, in particular, a free carboxyl group or an esterified carboxyl group which can be split physiologically, for example an esterified carboxyl group which can be split enzymatically.

Esterified carboxyl groups which can be split physiologically are, above all, those which can be split enzymatically or be split by the acid gastric juice. These esters are readily resorbable in the organism and can therefore be used therapeutically as such. Esters of this type are described, for example, in British Patent Specification 1,229,453, in Belgian Patent 789,821 and in German Patent Applications DT 1,951,012, DT 2,228,012 and DT 2,230,620. Such esters are derived, for example, from 5-hydroxyindanol or 3,4-benzo-5-oxo-tetrahydro-2-furanol or from alcohols of the formula $HO-CH_2OCO-R_2'$, wherein $R_2'$ can represent an alkyl radical or aminoalkyl radical or a cycloalkyl radical with 3-7 carbon atoms. In particular, $R_2'$ denotes a lower alkyl radical, such as methyl, ethyl, isopropyl and above all tert.butyl, an α-amino-lower alkyl radical, such as 1-amino-2-methylpropyl or 1-amino-3-methylbutyl, a cyclopentyl radical or a cyclohexyl radical.

The radical $R_3$ represents a hydrogen atom, lower alkoxy, especially methoxy (compare Netherlands Application No. 73/09,136) or an unsubstituted or substituted methyl group. Substituents of the methyl group are, above all, free, esterified or etherified hydroxyl or mercapto groups, optionally N-substituted carbamoyloxy or thiocarbamoylmercapto groups, or quaternary ammonium groups.

An esterified hydroxyl or mercapto group in a substituted methyl group $R_3$ contains, as the acid radical, above all the radical of a carboxylic acid or thiocarboxylic acid, for example lower alkanoyl which is optionally substituted by halogen atoms, especially chlorine, such as formyl, propionyl, butyryl, pivaloyl, or chloroacetyl, but especially acetyl, or aroyl or aryl-lower alkanoyl optionally substituted by, for example, lower alkyl, lower alkoxy, halogen or nitro, for example benzoyl or phenylacetyl, and also, as a thiocarbonic acid radical, in particular thioaroyl which is optionally substituted as mentioned, and above all thiobenzoyl. Esterified mercapto groups can in particular also contain heteroyl, wherein the heterocyclyl radical preferably contains 5-6 ring members and, as hetero-atoms, nitrogen, optionally in the N-oxidised form, and/or oxygen or sulphur, for example optionally 1-oxidised pyridyl, pyrimidyl, pyridazinyl, thiadiazolyl, oxadiazolyl or N-methyltetrazolyl. In addition, hydroxyl groups esterified by hydrogen halide acids should be mentioned; the methyl group can therefore be substituted by, for example, fluorine, chlorine or bromine.

Etherified hydroxyl groups in a substituted methyl group $R_3$ are described, for example, in Belgian Patent 719,710. Lower alkoxy, such as methoxy, ethoxy or n-propoxy, should be singled out.

Etherified mercapto groups in a substituted methyl group $R_3$ for example contain, as the etherifying radicals, lower alkyl, for example methyl, and also optionally substituted phenyl or heterocyclyl. Phenyl can be substituted by, for example, lower alkyl, lower alkoxy, halogen or nitro. The heterocyclyl radicals preferably have 5-6 ring members and contain, as hetero-atoms, nitrogen, optionally in the N-oxidised form, and/or oxygen or sulphur. Examples to be mentioned are optionally 1-oxidised pyridyl, pyrimidyl, pyridazinyl, pyrazinyl, imidazolyl, imidazolidyl, purinyl, triazolyl or tetrazolyl. These radicals can be substituted, for example, by lower alkyl, lower alkoxy, hydroxyl or halogen. Optionally substituted heterocyclyl radicals of aromatic character, with 5 ring atoms which comprise 2 nitrogen atoms and a further oxygen or sulphur atom or 1 to 2 further nitrogen atoms, should be singled out particularly. Preferred substituents are lower alkyl radicals with 1-5 carbon atoms such as methyl, ethyl, propyl, isopropyl, n-butyl, isobutyl and tert.butyl, lower alkoxy and lower alkylthio radicals with 1-5 carbon atoms, particularly methylthio, cycloalkyl radicals with 3-7 carbon atoms, for example cyclopentyl or cyclohexyl, or aryl radicals, such as phenyl or substituted phenyl, for example phenyl substituted by one or more nitro groups or halogen atoms or lower alkyl or lower alkoxy groups, or unsubstituted or substituted thienyl, particularly 2-thienyl, or thienyl substituted as indicated for phenyl, or optionally monosubstituted or disubstituted amino groups, for example acetylamino, tert. butoxycarbonylamino, tert.-amyloxycarbonylamino and sulphonylamino.

The following should be mentioned as examples of the heterocyclyl radical which etherifies the mercapto group: Triazolyl optionally substituted by lower alkyl and/or aryl, for example phenyl, such as 1-methyl-1H-1,2,3-triazol-4-yl, 1H-1,2,4-triazol-3-yl, 5-methyl-1H-1,2,4-triazol-3-yl, 3-methyl-1-phenyl-1H-1,2,4-triazol-5-yl, 4,5-dimethyl-4H-1,2,4-triazol-3-yl and 4-phenyl-4H-1,2,4-triazol-3-yl, tetrazolyl optionally substituted by lower alkyl or aryl, such as phenyl or chlorophenyl, such as 1H-tetrazol-5-yl, 1-methyl-1H-tetrazol-5-yl, 1-ethyl-1H-tetrazol-5-yl, 1-n-propyl-1H-tetrazol-5-yl, 1-phenyl-1H-tetrazol-5-yl and 1-p-chlorophenyl-1-H-tetrazol-5-yl, 2-thiazolyl, thiazolyl optionally substituted by lower alkyl, such as 4-(2-thienyl)-2-thiazolyl and 4,5-dimethyl-2-thiazolyl, thiadiazolyl optionally substituted by lower alkyl, such as 1,3,4-thiadiazol-2-yl, 2-methyl-1,3,4-thiadrazol-5-yl, 2-ethyl-1,3,4-thiadiazol-5-yl, 2-n-propyl-1,3,4-thiadiazol-5-yl and 2-isopropyl-1,3,4-thiadiazol-5-yl, 5-thiatriazolyl, oxazolyl, isoxazolyl or oxadiazolyl optionally substituted by lower alkyl and/or aryl, such as 5-oxazolyl, 4-methyl-5-oxazolyl, 2-oxazolyl, 4,5-diphenyl-2-oxazolyl, 3-methyl-5-isoxazolyl, 1,2,4-oxadiazol-5-yl, 2-methyl-1,3,4-oxadiazol-5-yl, 2-phenyl-1,3,4-oxadiazol-5-yl, 5-p-nitrophenyl-1,3,4-oxadiazol-2-yl and 2-(2-thienyl)-1,3,4-oxadiazol-5-yl, as well as bicyclic heterocyclyl radicals which are optionally substituted by halogen or nitro, such as 2-benzimidazolyl, 5-chloro-2-benzimidazolyl, 2-benzoxazolyl, 5-nitro-2-benzoxazolyl, 5-chloro-2-benzoxazolyl, s-triazolo[4.3-a]pyrid-3-yl, 3H-v-triazolo[4,5-b]pyrid-5-y, purin-2-yl, purin-6-yl and 8-chloro-2-methylpurin-6-yl.

An optionally N-substituted carbamoyloxy group or thiocarbamolymercapto group in a substituted methyl group $R_3$ is, for example, a group of the formula -O-CO-NH-$R_{II}$ (French Pat. No. 1,463,831) or

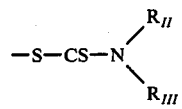

wherein $R_{II}$ is hydrogen or an optionally halogen-substituted lower alkyl radical and $R_{III}$ is hydrogen or $R_{II}$ [compare J. Med. Chem. 8, 174 (1965)]. Above all, $R_{II}$ is methyl, ethyl or chlorine-substituted methyl or ethyl, especially β-chloroethyl.

In a quaternary ammonium-methyl group $R_3$, the ammonium part is preferably an unsubstituted or substituted pyridinium group.

Examples of substitutents of the pyridinium group which should be mentioned are those listed in Antimicrobial Agents and Chemotherapy 1966, page 573-580, such as unsubstituted or substituted, for example hydroxyl-substituted or carboxyl-substituted, lower alkyl, for example methyl, ethyl, propyl, hydroxymethyl, carboxymethyl, halogen, such as fluorine, chlorine, bromine or iodine, or trifluoromethyl, hydroxyl, sulpho, carboxyl, cyano, lower alkoxycarbonyl, such as methoxycarbonyl, or ethoxycarbonyl, lower alkylcarbonyl, such as methycarbonyl, and, in particular carboamoyl which is unsubstituted or substituted, for example by lower alkyl, hydroxy-lower alkyl or halogeno-lower alkyl, especially chloro-lower alkyl, such as N-methylcarbamoyl, N-isopropylcarbamoyl and N-β-chloroethylcarbamoyl, but above all carbamoyl. The substituents can be in the 2-, 3- and/or 4-position but are preferably in the 3- or 4-position.

The radical B can be monocyclic, bicyclic or tricyclic and in particular comprises optionally polysubstituted and/or optionally partially hydrogenated pyridine, pyrazine, pyrimidine, pyridazine, triazine, quinoline, isoquinoline, napthyridine or pyrido-pyrimidine rings which are substituted at the nitrogen-containing ring by 1 or 2 optionally, in particular physiologically splittably, esterified, or etherified hydroxyl or mercapto groups or by optionally mono- or di-lower alkylated or lower alkanoylated amino groups or by halogen, and the tautomers of these rings.

Radicals B to be singled out for example have the formula (B₁)

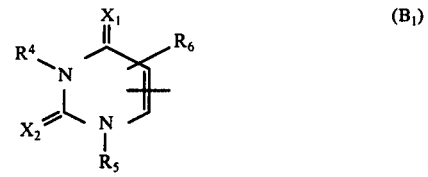

wherein $X_1$ and $X_2$ independently of one another denote oxygen, sulphur or the imino group =NH, $R_4$ and $R_5$ independently of one another denote hydrogen or lower alkyl, especially methyl, and $R_6$ denotes hydrogen, halogen, such as, in particular, chlorine, lower alkyl, especially methyl, or aryl, especially phenyl, or have the formula (B₂)

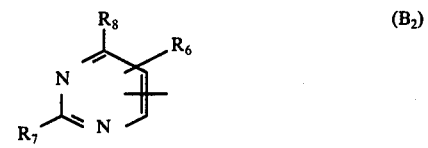

wherein $R_6$ denotes hydrogen, halogen, especially chlorine, lower alkyl, especially methyl, or aryl, especially phenyl, and $R_7$ and $R_8$ independently of one another denote a free hydroxyl or mercapto group, an etherified hydroxyl or mercapto group, such as a lower alkylated, for example methylated, hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, or halogen, such as chlorine, or a mono- or di-lower alkylated, or acylated, such as lower alkanoylated, amino group, and one of the radicals $R_7$ or $R_8$ can also be hydrogen, or have the formula (B₃)

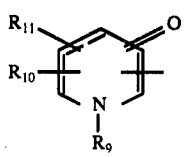

wherein R₉ denotes hydrogen or lower alkyl, especially methyl, and R₁₀ and R₁₁ substitute adjoining ring carbon atoms and together represent a lower alkylene radical, especially a 1,3-propylene, 1,4-butylene or 1,5-pentylene radical, which optionally carries an oxo group, or a radical of the formula

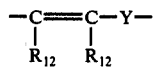

wherein Y denotes the grouping —CH=N— or —CH=CH— and the two R₁₂ each denote a hydrogen atom, or one of the two denotes hydrogen and the other denotes hydroxyl, lower alkyl, especially methyl, lower alkoxy, especially methoxy, lower alkylmercapto, especially methylmercapto, lower alkanoyl, especially acetyl, lower alkanoylamido, especially acetylamido, lower alkoxycarbonyloxy, especially ethoxycarbonyloxy, lower alkylsulphonyl, especially methylsulphonyl, or aryl, especially phenyl, or the two R₁₂ together with the —CH=CH— group form a thiazole, isothiazole, pyrrole, furane or benzene ring which can be substituted by an oxo group, a lower alkyl group, such as a methyl group, or a lower alkanoyl group, such as an acetyl group, and wherein the broken line denotes a 4,5-or 5,6-double bond, or have the formula (B₄)

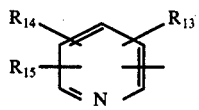

wherein R₁₃ denotes a free hydroxyl or mercapto group, an etherified hydroxyl or mercapto group, such as a lower alkylated, for example methylated, hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, a mono- or di-lower alkylated, such as methylated, or lower alkanoylated, such as acetylated, amino group, or halogen, especially chlorine, R₁₄ represents hydrogen, hydroxyl, nitrile, lower alkyl, such as methyl, hydroxy-lower alkyl, such as 1-hydroxyethyl, lower alkanoyl, such as acetyl, aryl, especially phenyl, or arylcarbonyl, especially phenylcarbonyl, R₁₅ represents hydrogen, nitrile, lower alkyl, especially methyl, lower alkanoyl, especially acetyl, or aryl, especially phenyl, or R₁₄ and R₁₅ substitute adjacent ring carbon atoms and together represent a radical of the formula

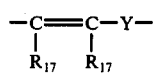

wherein Y denotes the grouping —CH=CH— or —CH=N— and one R₁₇ denotes hydrogen and the other denotes hydroxyl, optionally halogenated lower alkyl, such as methyl or trifluoromethyl, lower alkoxy, such as ethoxy, lower alkanoyloxy, such as acetoxy, mercapto, lower alkylmercapto, especially methylmercapto, amino, mono- or di-lower alkylamino, such as dimethylamino, lower alkanoylamido, such as acetamido, optionally phenyl-substituted lower alkoxycarbonylamido, such as ethoxycarbonylamido or benzyloxycarbonylamido, or lower alkylsulphonyl, especially methylsulphonyl, or the two R₁₇ together denote the methylenedioxy group or a lower alkylene radical, especially the 1,3-propylene, 1,4-butylene or 1,5-pentylene radical, or R₁₄ and R₁₅ together represent a group of the formula

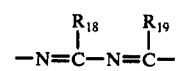

wherein R₁₈ denotes hydrogen, hydroxyl or lower alkyl, especially methyl, lower alkoxy, especially methoxy, amino, mono- or di-lower alkylamino, especially dimethylamino or optionally phenyl-substituted lower alkoxycarbonylamido, such as ethoxycarbonylamido or benzyloxycarbonylamido, and R₁₉ denotes hydrogen, lower alkyl, especially methyl, or lower alkoxy, especially methoxy, or having the formula (B₅)

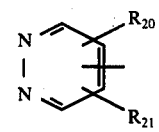

wherein R₂₀ denotes a free hydroxyl or mercapto or mercapto group, an etherified hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, and R₂₁ denotes hydrogen, hydroxyl, halogen, especially chlorine, or lower alkyl, especially methyl, or have the formula (B₆)

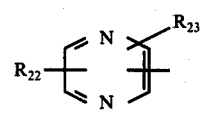

wherein R₂₂ denotes a free hydroxyl or mercapto group, an etherified, especially lower alkylated, such as methylated, hydroxyl or mercapto group, or an esterified hydroxyl or mercapto group, especially a physiologically splittable esterified hydroxy or mercapto group, such as a hydroxyl or mercapto group esterified with a half-ester of carbonic acid, for example monoethyl carbonate, and R₂₃ denotes hydrogen, hydroxyl, halogen, especially chlorine, or lower alkyl, especially methyl, or have the formula (B₇)

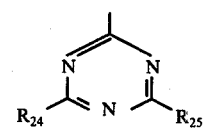

wherein R₂₄ and R₂₅ independently of one another denote hydrogen, halogen, especially chlorine, a free hydroxyl or mercapto group, an etherified, especially lower alkylated, such as methylated, hydroxyl or mercapto group, or an esterified, hydroxyl or mercapto group, especially a physiologically splittable esterified hydroxyl or mercapto group, such as a hydroxyl or mercapto group esterified with a half-ester of carbonic acid, for example monoethyl carbonate, or an optionally mono- or di-lower alkylated, especially dimethylated, or a lower alkanoylated, such as acetylated, amino group, or have the formula (B₈)

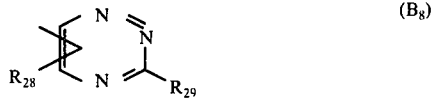

wherein R₂₈ and R₂₉ independently of one another denote hydrogen, halogen, especially chlorine, or each an etherified hydroxyl or mercapto group, especially a lower alkylated, such as methylated, or benzylated, hydroxyl or mercapto group, or an esterified hydroxyl or mercapto group, especially a physiologically splittable esterified hydroxyl or mercapto group, such as a hydroxyl or mercapto group esterified with a half-ester of carbonic acid, for example monoethyl carbonate, or, in particular, a free hydroxyl or mercapto group or a mono- or di-lower alkylated, especially dimethylated, or a lower alkanoylated, such as acetylated, amino group or in particular a free amino group, the substituent R₂₈ preferably occupying the 5-position of the as-triazine ring, or have, where appropriate, a formula tautomeric thereto.

Above all, the invention relates to the compounds of the formula I, wherein R₁ has the meaning mentioned under the formula I and in particular R₁ represents phenyl, R₂ denotes a carboxyl group, R₃ denotes hydrogen, methoxy, acetoxymethyl, pyridiniomethyl or 1-methyl-1H-tetrazol-5-ylthiomethyl and the group B denotes one of the groups B₁ to B₈, in particular a group B₁, B₃, B₅ or B₈ which is exclusively monosubstituted or disubstituted by mercapto or, above all, by hydroxyl or oxo, and wherein the hydroxyl or mercapto groups are present either in an esterified form which can be split physiologically, especially in the form of their esters with a monolower alkylcarbonate or, in particular, in the free form.

Compounds to be singled out particularly are those of the formula I, wherein R₁ represents phenyl, R₂ denotes a carboxyl group, R₃ denotes acetoxymethyl, pyridiniomethyl or 1-methyl-1H-tetrazol-5-ylthiomethyl and the group B denotes the 2,4-dioxo-1,2,3,4-tetrahydropyrimid-5-yl, 2,6-dioxo-1,2,3,6-tetrahydropyrimid-4-yl, 1,6-dihydro-6-oxo-3-pyridazinyl, 2-hydroxy-5-pyridyl, 2-hydroxy-4-quinolyl or 3,5-dioxo-2,3,4,5-tetrahydro-1,2,4-triazin-6-yl radical, and their salts. Preferred compounds of the formula I are those which are derived from D(−)-mandelic acid, for example 7β-[D(−)-(2,6-dioxo-1,2,3,6-tetrahydro-4-pyrimidinecarbonyloxy)-phenyl-acetamido]-cephalosporanic acid, 7β-[D(−)-α(2,4-dioxo-1,2,3,4-tetrahydro-5-pyrimidinecarbonyloxy)-phenylacetamido]-cephalosporanic acid, 7β-[D(−)-α-(2-hydroxy-5-pyridinecarbonyloxy)-phenylacetamido]-cephalosporanic acid, 7β-[D(−)-α-(3-hydroxy-2-pyridinecarbonyloxy)-phenylacetamido]-cephalosporanic acid, 7β-[D(−)-α-(2-hydroxy-4-quinolinecarbonyloxy)-phenylacetamido]-cephalosporanic acid, 7β-[D(−)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid, 7β-[D(−)-α-(1,6-dihydro-6-oxo-3-pyridazinecarbonyloxy)-phenylacetamido]-cephalosporanic acid, 7β-[D(−)-α-(1,6-dihydro-6-oxo-3-pyridazinecarbonyloxy)-phenylacetamido]-3-[(1-methyl-1H-tetrazol-5-yl)-thiomethyl]-ceph-3-em-4-carboxylic acid and 7β-[D(−)-α-(3,5-dioxo-2,3,4,5-tetrahydro-1,2,4-triazine-6-carbonyloxy)-phenylacetamido]-cephalosporanic acid.

Salts of compounds of the present invention are, above all, pharmaceutically usable non-toxic salts of compounds which are able to form salts with bases. Such salts are, above all, metal salts or ammonium salts, such as alkali metal salts or alkaline earth metal salts, for example sodium, potassium, magnesium, calcium or aluminium salts, as well as ammonium salts with ammonia or suitable organic amines, the amines used for forming the salt being above all aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aminoacids such as lysine, ornithine and arginine, basic aliphatic esters of carboxylic acids, for example 4-aminobenzoic acid 2-diethylaminoethyl ester, lower alkyleneamines, for example 1-ethylpiperidine, cycloalkylamines, for example bicyclohexylamine, or benzylamines, for example N,N'-dibenzyl-ethylenediamine, and also bases of the pyridine type, for example pyridine, collidine or quinoline.

Further salts are derived from the compounds according to the invention which have a basic group, for example an unsubstituted or monoalkylated or dialkylated amino group. Such compounds either form inner salts with a free carboxyl group R₂, or can be converted into a salt with a pharmaceutically usable, non-toxic organic or inorganic acid. Suitable acids are organic carboxylic acids or sulphonic acids, for example alkanoic acids, such as trifluoroacetic acid, or methanesulphonic acid, or aromatic acids, such as benzoic acid or benzenesulphonic acid, or inorganic acids, such as hydrochloric acid, sulphuric acid or phosphoric acid.

The new compounds can be in the form of mixtures of isomers, for example racemates, or in the form of individual isomers, for example optically active antipodes.

The new compounds of the formula I exhibit a pharmacological action, in particular an especially pronounced antibacterial action. Thus, they are active against Gram-negative bacteria, such as enterobacteriaceae, for example Salmonellae, strains of Escherichia and especially strains of Proteus, and also against Gram-positive bacteria, such as staphylococci. For example, they inhibit the growth of enterobacteriaceae and staphylococci in vitro at dilutions of down to about 0.2-30 μg/ml. In mice, they are active, on subcutaneous administration, against staphylococci, such as Staphylococcus aureus, in a dosage range of about 8 to about 20 mg/kg, and against enterobacteriaceae, such as Escherichia coli, Salmonella typhimurium and Proteus species, in a dosage range of about 15 to about 300 mg/kg. They can therefore be used for combating infections which are caused by such microorganisms, and also as feedingstuff additives, for the preservation of foodstuffs or as disinfectants.

The compounds of the present invention are manufactured according to methods which are in themselves known. They can be manufactured, for example, by a) acylating a compound of the formula (II)

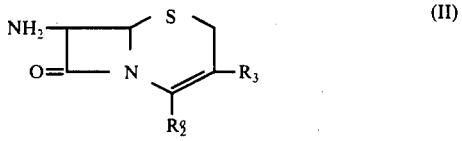

wherein $R_2^o$ has the meaning of $R_2$ or represents an easily splittable esterified carboxyl group, and $R_3$ has the indicated meaning, or a salt thereof, with a carboxylic acid of the formula (III)

wherein $R_1$ and B have the abovementioned meanings, or with a reactive functional derivative thereof, or b) acylating a compound of the formula IV

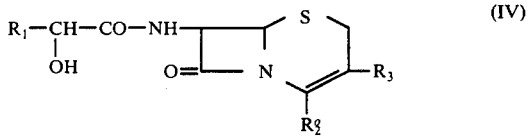

wherein $R_1$ has the abovementioned meaning, $R_2^o$ has the meaning of $R_2$ or represents an easily splittable esterified carboxyl group and $R_3$ has the abovementioned meaning, or a salt thereof, with an acid of the formula B—COOH (V), wherein B has the abovementioned meaning, or with a reactive functional derivative thereof, and, if appropriate, in a resulting compound splitting off a protective group and/or converting an easily splittable esterified carboxyl group $R_2^o$ into a free or physiologically splittable esterified carboxyl group $R_2$, and/or, if desired, converting an optionally substituted methyl group $R_3$ into another group $R_3$ and/or, if desired, converting a compound obtained as the free acid into a salt or a salt obtained into the free acid and-/or separating an isomer mixture obtained into the individual isomers.

An easily splittable esterified carboxyl group $R_2^o$ in a starting material of the formula II or IV is, in particular, an ester group which can be split to the free carboxyl group in a neutral, acid or weakly alkaline medium, solvolytically, for example hydrolytically, alcoholytically or acidolytically, or reductively, for example hydrogenolytically.

Esterified carboxyl groups $R_2^o$ which can easily be split by solvolysis with a solvent containing hydroxyl groups, for example water or alcohols, such as, for example, methanol or ethanol, preferably under neutral conditions, are above all those which are derived from silyl alcohol or stannyl alcohol. Such groups are described, for example, in British Patent Specifications 1,073,530 and 1,211,694 and in German Offenlegungsschrift 1,800,698. Examples which may be mentioned are tri-lower alkyl-silyloxycarbonyl, such as trimethyl-silyloxycarbonyl and tert.-butyl-dimethyl-silyloxy-carbonyl, lower alkoxy-lower alkyl-halogeno-silyloxycarbonyl, for example chloro-methoxy-methyl-silyloxycarbonyl, or tri-lower alkyl-stannyloxycarbonyl, for example tri-n-butyl-stannyloxycarbonyl.

Esterified carboxyl groups $R_2^o$ which are split easily by acidolysis, for example in the presence of hydrogen chloride, hydrogen fluoride or hydrogen bromide or of organic acids, such as acetic acid, trifluoroacetic acid or formic acid, if appropriate with the addition of a nucleophilic compound, such as phenol or anisole, are derived from lower alkanols which are poly-branched in the α-position or lower alkanols which contain one or more electron donors in the α-position. Examples of such esterified carboxyl groups are tert.butoxycarbonyl, tert.amyloxycarbonyl, cyclopentyloxycarbonyl, cyclohexyloxycarbonyl, adamantyloxycarbonyl, furfuryloxycarbonyl, p-methoxy-benzyloxycarbonyl, diphenylmethoxycarbonyl and pivaloyloxymethoxycarbonyl. Esterified carboxyl groups $R_2^o$ which can be split by reduction, for example with zinc and acid, are above all derived from 2-halogeno-lower alkanols, for example from 2,2,2-trichloroethanol, 2-bromoethanol and 2-iodoethanol. Carboxyl groups $R_2^o$ esterified by phenacyl alcohol or p-nitrobenzyl alcohol can be split by hydrogenolysis, for example by treatment with nascent hydrogen or with hydrogen in the presence of a noble metal catalyst, for example a palladium catalyst.

Salts of starting materials of the formula II or IV are, in particular, salts of those compounds which have a free carboxyl group, above all ammonium salts, such as tri-lower alkylammonium salts, for example triethylammonium salts, and also alkali metal salts.

The acylation of the amino group of the compound II with the carboxylic acid of the formula III is carried out in accordance with methods which are in themselves known, in particular in the manner known from penicillin chemistry and cephalosporin chemistry for the acylation of weakly basic amino groups. The acylating agent used is either the corresponding acid of the formula III, in which case the reaction is carried out in the presence of a condensation agent, for example a carbodiimide, such as N,N'-diethyl-, N,N'-dipropyl-, N,N'-diisopropyl-, N,N'-dicyclohexyl- or N-ethyl-N'-γ-dimethylamino-propylcarbodiimide, or in the presence of a suitable carbonyl compound, for example N,N'-carbonyldiimidazole, or of isoxazolium salts, for example N-ethyl-5-phenyl-isoxazolinium-3'-sulphonate or N-tert.butyl-5-methyl-isoxazolinium perchlorate, or of an acylamino compound, for example 2-ethoxy-1-ethoxycarbonyl-1,2-dihydroquinoline, or is a reactive functional derivative, above all an acid halide, especially an acid chloride or acid bromide, or, for example, an activated ester, for example a p-nitrophenyl ester, 2,4-dinitrophenyl ester, 2,4,5- or 2,4,6-trichlorophenyl ester or pentachlorophenyl ester or, for example, the cyanomethyl ester, N-hydroxysuccinimide ester, N-hydroxypiperidine ester or N-hydroxyphthalimide ester, or a mixed anhydride, for example a mixed anhydride with mono-esterified carbonic acid, such as a carbonic acid lower alkyl ester, for example the ethyl ester or methyl ester, or a mixed anhydride with an optionally halogen-substituted lower alkanoic acid such as formic acid, pivalic acid or trichloroacetic acid, in which case the reaction is carried out in the presence of a catalyst and-/or in the presence of basic agents such as aliphatic, aromatic or heterocyclic nitrogen bases, for example triethylamine, diisopropylethylamine, N,N-diethylaminoacetic acid ethyl ester, N-methylmorpholine, N,N-dimethylaniline, pyridine, 2-hydroxypyridine, p-dimethylaminopyridine, collidine or 2,6-lutidine.

The acylation of the hydroxyl group of the compound IV with the carboxylic acid of the formula V is also carried out in a manner which is in itself known. The acylating agent used is either this carboxylic acid itself or a halide thereof, especially a chloride, or a mixed anhydride, for example a mixed anhydride with a mono-esterified carbonic acid, such as a carbonic acid lower alkyl ester, for example ethyl ester or methyl ester. If a hydroxyl group is present in the α-position relative to the carboxyl group in the group B, a mixed inner anhydride having the partial formula

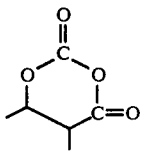
(VI)

can also be used for the acylation. The acylation with the carboxylic acid itself is carried out in the presence of one of the condensation agents mentioned, especially of N,N'-carbonyldiimidazole or N,N'-dicyclohexylcarbodiimide. If a mixed anhydride is employed, one of the bases mentioned, for example triethylamine, is used as a condensation agent.

The solvents or diluents used in the above methods of acylation for the manufacture of the compounds according to the invention are inert liquids, for example carboxylic acid amides, such as N,N-di-lower alkylamides, for example dimethylformamide, halogenated hydrocarbons, for example methylene chloride, carbon tetrachloride or chlorobenzene, ketones, for example acetone, esters, for example ethyl acetate, nitriles, for example acetonitrile, solvents containing oxa groups, such as tetrahydrofurane and dioxane, or mixtures thereof.

The reaction is carried out at room temperature or with cooling or warming, for example at temperatures of −70° to +100° C, preferably at about −20° to +30° C, if appropriate in an inert gas atmosphere, for example a nitrogen atmosphere, and/or with exclusion of moisture.

In carrying out the acylation, free hydroxyl and/or mercapto groups which may be present in the reactants are preferably protected, especially by protective groups which can be split off easily, such as are known, for example, from the synthesis of peptides, compare Schröder and Lübke "The Peptides," vol. 1, Academic Press, New York and London, 1965, and Th. Wieland, Angew. Chem. 63 (1951) 7-14, 66 (1954), 507-512, 69 (1957), 362-372, 71 (1959), 417-425 and 75 (1963). Hydroxyl groups or mercapto groups can be protected by etherification, for example with tert.butanol, or in the form of a silyl ether, such as a trityl ether, or in the form of a stannyl ether, or by esterification, for example with a half-ester of a carbonic acid half-halide, such as ethoxycarbonyl chloride.

In a compound obtained according to the invention, a protected carboxyl group $R_2^o$, especially an esterified carboxyl group which can easily be converted into the free carboxyl group, can be converted to the free carboxyl group solvolytically or reductively, in the manner indicated above.

In resulting compounds of the formula I, a substituted methyl group can be converted into another group of this type. Thus, for example, a compound containing an esterified hydroxymethylradical $R_3$, wherein the esterified hydroxyl group in particular denotes lower alkanoyloxy, for example acetoxy, can first be reacted with thiobenzoic acid and then be treated with pyridine in the presence of a mercury salt, or can be reacted with a suitable salt, such as potassium thiocyanate, potassium iodide or potassium nitrate, and with pyridine in the presence of water at a pH value of about 6.5, obtained, for example, by means of phosphoric acid, thus giving the corresponding pyridiniummethyl compound which can, if required, be converted to the inner salt (the zwitter ion form), for example by treatment with a suitable ion exchange reagent. The pyridinium compound can also be manufactured in accordance with the process of Belgian Pat. No. 719,711 (DOS 1,795,643) by first converting the acetoxy group into a group more suitable for nucleophilic exchange, for example a halogen atom or an acetoxy group which contains an electron-attracting substituent, such as, for example, chloroacetoxy, dichloroacetoxy or cyanoacetoxy. Furthermore, compounds containing a lower alkanoyloxymethyl group, for example an acetoxymethyl group, as the radical $R_3$ can be reacted with a mercapto compound, such as an optionally substituted lower alkylmercaptan, phenylmercaptan or heterocyclylmercaptan, thus giving compounds of the formula I, wherein $R_3$ represents an etherified mercaptomethyl group.

Salts of compounds of the formula I can be manufactured in a manner which is in itself known. Thus, salts of compounds of the formula I, wherein $R_2$ represents a free carboxyl group, can be formed, for example, by treatment with metal compounds, such as alkali metal salts of suitable carboxylic acids, for example with the sodium salt of α-ethyl-caproic acid, or with ammonia or a suitable organic amine.

Salts can be converted into the free compounds in the usual manner, metal salts and ammonium salts, for example by treatment with suitable acids or ion exchangers.

Resulting mixtures of isomers can be separated into the individual isomers according to methods which are in themselves known, for example by fractional crystallisation, adsorption chromatography (column chromatography or thin layer chromatography) or other suitable methods of separation. Resulting racemates can be separated into the antipodes in the usual manner, if appropriate after the introduction of suitable salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also embraces those embodiments according to which compounds obtained as intermediates are used as starting materials and the remaining process steps are carried out with these, or the process is discontinued at any stage; furthermore, starting materials can be used in the form of derivatives or be formed during the reaction.

Preferably, those starting materials are used, and the reaction conditions are so chosen, that the compounds mentioned initially as being particularly preferred are obtained.

The starting materials of the formula II and IV are known or can be manufactured according to known processes.

Compounds of the formula III and their reactive functional derivatives have not previously been disclosed. They can be obtained in a manner which is in itself known, by acylating a compound of the formula $R_1$—CH(OH)—COOH (VII), in which the carboxyl group is present in a protected form, for example in the form of an easily splittable esterified carboxyl group, with a carboxylic acid of the formula B—COOH (V), with a halide thereof or with a mixed anhydride thereof, then splitting off the carboxyl protective group and, if desired, converting the carboxylic acid obtained into a reactive functional derivative thereof.

Easily splittable esters of carboxylic acids of the formula VII are, in particular, those which after acylation of the hydroxyl group can be split solvolytically, for example hydrolytically, alcoholytically or especially acidolytically, or reductively, to give the free carboxylic acid of the formula III. Such easily splittable ester groups are derived from the same alcohols from which the easily splittable esterified carboxyl groups $R_2^o$ are derived, and the subsequent splitting is carried out analogously.

The acylation of the hydroxyl group in a compound of the formula (VII), in which the carboxyl group is protected, is carried out analogously to the acylation of the hydroxyl group in a compound of the formula (IV). The acylating agent used is either the corresponding acid of the formula V, in which case the reaction is carried out in the presence of a condensation agent, for example a carbodiimide, such as N,N'-diethyl-, N,N'-dipropyl-, N,N'-diisopropyl-, N,N'-dicyclohexyl- or N-ethyl-N'-γ-dimethylamino-propylcarbodiimide, or of a suitable carbonyl compound, for example N,N'-carbonyldiimidazole, or of isoxazolium salts, for example N-ethyl-5-phenyl-isoxazolinium-3'-sulphonate and N-tert.butyl-5-methyl-isoxazolinium perchlorate, or of an acylamino compound, for example 2-ethoxy-1-ethoxycarbonyl-1,2-dihydroquinoline, or is a reactive functional derivative, above all an acid halide, especially an acid chloride or acid bromide, or, for example, an activated ester, for example a p-nitrophenyl ester, 2,4-dinitrophenyl ester, 2,4,5- or 2,4,6-trichlorophenyl ester or pentachlorophenyl ester, or, for example, the cyanomethyl ester, N-hydroxy-succinimide ester, N-hydroxypiperidine ester or N-hydroxyphthalimide ester, or a mixed anhydride, for example with a mono-esterified carbonic acid, such as a carbonic acid lower alkyl ester, for example ethyl ester or methyl ester, or with an optionally halogen-substituted lower alkanoic acid such as formic acid, pivalic acid or trichloroacetic acid, in which case the reaction is carried out in the presence of basic agents such as aliphatic, aromatic or heterocyclic nitrogen bases, for example triethylamine, diisopropylethylamine, N,N-diethylaminoacetic acid ethyl ester, N-methylmorpholine, N,N-dimethylaniline, pyridine, 2-hydroxypyridine, p-dimethylaminopyridine, collidine or 2,6-lutidine, but especially an excess of pyridine.

If, in the group B, there is a hydroxyl group in the α-position relative to the carboxyl group, it is also possible to use a mixed inner anhydride of the partial formula

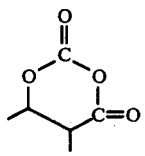

(VI)

for the acylation.

The solvents or diluents used in the above methods of acylation for the manufacture of compounds of the formula III are inert liquids, for example carboxylic acid amides, such as N,N-di-lower alkylamides, for example dimethylformamide, halogenated hydrocarbons, for example methylene chloride, carbon tetrachloride or chlorobenzene, ketones, for example acetone, esters, for example ethyl acetate, nitriles, for example acetonitrile, solvents containing oxa groups, such as tetrahydrofurane and dioxane, or N-alkylated phosphoric acid amides, such as hexamethylphosphoric acid triamide, or mixtures thereof.

The reaction is carried out at room temperature or with cooling or warming, for example at temperatures of −70° to +100° C, preferably at about −20° to +30° C, if appropriate in an inert gas atmosphere, for example a nitrogen atmosphere, and/or with exclusion of moisture.

In the acylation of compounds of the formula (VII) it is again possible to protect free hydroxyl and/or mercapto groups which may be present in the reactant of the formula (V), especially by protective groups which can easily be split off, such as are known, for example, from the synthesis of peptides, compare Schröder and Lübke "The Peptides," vol. 1, Academic Press, New York and London, 1965, and Th. Wieland, Angew. Chem. 63 (1951) 7–14, 66 (1954), 507–512, 69, (1957), 362–372, 71 (1959), 417–425 and 75 (1963). Hydroxyl groups or mercapto groups can be protected by etherification, for example with tert.butanol, or in the form of a silyl ether, such as a trityl ether, or of a stannyl ether, or by esterification, for example with a half-ester of a carbonic acid half-halide, such as ethoxycarbonyl chloride.

The conversion of a resulting carboxylic acid of the formula (III) into a reactive functional derivative thereof is carried out in a manner which is in itself known. Carboxylic acid chlorides are obtained, for example, by treatment with thionyl chloride, activated esters are obtained, for example, by reaction of this resulting carboxylic acid chloride with an appropriate hydroxy compound, for example p-nitrophenol or N-hydroxyphthalimide, and mixed anhydrides are obtained by reaction of a carboxylic acid of the formula (III) with an appropriate halide, for example chloride, of a second carboxylic acid, for example a mono-esterified carbonic acid, such as a carbonic acid lower alkyl ester, for example the ethyl ester or methyl ester, or an optionally halogen-substituted lower alkanoic acid, such as formic acid, pivalic acid or trichloroacetic acid. When forming the mixed anhydride, a simultaneously present hydroxyl or mercapto group in the radical B can, if appropriate, be esterified by the carboxylic acid halide used, for example by the ethoxycarbonyl radical when using chloroformic acid ethyl ester.

The new compounds can be used as medicaments, for example in the form of pharmaceutical preparations which contain an effective amount of the active substance together with, or mixed with, inorganic or organic, solid or liquid, pharmaceutically usable excipients which are suitable for enteral or, preferably, parenteral administration. Thus, tablets or gelatine capsules are used, which contain the active compound together with excipients, for example lactose, sucrose, mannitol, sorbitol or cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Preferably, the pharmacologically active compounds of the present invention are used in the form of injectable preparations, for example intravenously administrable preparations, or of infusion solutions. Such solutions are, preferably, isotonic aqueous solutions or suspensions and these can be prepared before use, for example from lyophilised preparations which contain the active compound by itself or together with an excipient, for example mannitol. The pharmacological preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which, if desired, can contain further pharmacologically valuable materials, are produced in a manner which is in itself known, for example by means of conventional mixing, granulating, dragee-making, dissolving or lyophilising processes, and contain from about 0.1 to 100%, especially from about 1 to about 50%, of lyophilisates up to 100% of the active compound.

In the context of the present description, organic radicals described as "lower" contain up to 7, preferably up to 4, carbon atoms; acyl radicals contain up to 20, preferably up to 12, carbon atoms.

The examples which follow serve to illustrate the invention.

The following systems are used in the thin layer chromatography employed:

System 52 A—n-butanol/glacial acetic acid/water (67:10:23)

System 67—n-butanol/ethanol/water (40:10:50, upper phase)

System 101—n-butanol/pyridine/glacial acetic acid/water (38:24:8:30)

System 101A—n-butanol/pyridine/glacial acetic acid/water (42:24:4:30)

EXAMPLE 1

A solution of 2.70 g of 7β-[D(−)-α-(2,6-dioxo-1,2,3,6-tetrahydro-4-pyrimidinecarbonyloxy)-phenylacetamido]-cephalosporanic acid benzhydryl ester in a mixture of 10 ml of benzene and 0.41 ml of anisole is cooled to +5° C, 30 ml of trifluoroacetic acid are then added and the mixture is stirred for 10 minutes in an ice bath, whilst excluding atmospheric moisture. 300 ml of ether are then added to the reaction mixture and the product obtained is filtered off and washed with ether. The filter residue is mixed thoroughly with 50 ml of phosphate buffer solution of pH 7.5 and the mixture is extracted with ethyl acetate. The aqueous phase is separated off, cooled to +5° C in an ice bath, acidified (pH 2.5) by dropwise addition of 20% strength phosphoric acid, while stirring and cooling in an ice bath, and again extracted with ethyl acetate. The ethyl acetate extracts are combined, washed once with sodium chloride solution and dried over sodium sulphate, and the solvent is evaporated off on a rotary evaporator at 45° C. The 7β-[D(−)-α-(2,6-dioxo-1,2,3,6-tetrahydro-4-pyrimidinecarbonyloxy)-phenylacetamido]-cephalosporanic acid which remains is purified by crystallisation from ethyl acetate. Melting point: 170–172° C, with decomposition. Thin layer chromatogram on silica gel: $Rf_{52A}=0.32$; $Rf_{67}=0.20$; $Rf_{101}=0.50$; $Rf_{101A}=0.45$. $[\alpha]_D^{20} = +26° \pm 1°$ (c= 0.912 in dimethylsulphoxide).

The starting material can be prepared as follows:

A solution of 1.85 g of N,N'-dicyclohexyl-carbodiimide in 10 ml of tetrahydrofurane is added dropwise over the course of 10 minutes, whilst stirring at room temperature, to a solution of 2.90 g of D(−)-α-(2,6-dioxo-1,2,3,6-tetrahydro-4-pyrimidine-carbonyloxy)-phenylacetic acid [prepared by reaction of D(−)-mandelic acid with orotic acid chloride in tetrahydrofurane in the presence of pyridine; melting point: 133°–135° C, with decomposition, $[\alpha]_D^{20} = -112° \pm 1°$ (c= 0.975 in dimethylsulphoxide); thin layer chromatogram on silica gel: $Rf_{52A} = 0.44$] and 4.00 g of 7β-amino-cephalosporanic acid benzhydryl ester in 80 ml of tetrahydrofurane, and the reaction mixture is stirred for 2 hours at room temperature with exclusion of atmospheric moisture. A solution of 0.90 g of N,N'-dicyclohexyl-carbodiimide in 5 ml of tetrahydrofurane is then added dropwise to the suspension and stirring is continued. After a reaction time of a total of 6 hours, the suspension is filtered, the filter residue is washed with tetrahydrofurane, the filtrate is evaporated on a rotary evaporator at 40° C and the residue is taken up in ethyl acetate. The ethyl acetate solution is washed successively with water, 1N sodium bicarbonate solution and water and is dried over sodium sulphate, the ethyl acetate is evaporated off on a rotary evaporator at 45° C and the foam which remains is chromatographed on a 30-fold quantity of silica gel. 7β-[D(−)-α-(2,6-Dioxo-1,2,3,6-tetrahydro-4-pyrimidinecarbonyloxy)-phenylacetamido]-cephalosporanic acid benzhydryl ester is eluted with a mixture of methylene chloride and methyl acetate (7:3). Thin layer chromatogram on silica gel (running agent: toluene/ethanol (9:1)): Rf=0.29.

EXAMPLE 2

Using the process of Example 1, 7β-[D(−)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid is obtained by treating 7β-[D(−)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid benzhydryl ester (2.40 g) with trifluoroacetic acid (30 ml) in a mixture of methylene chloride (10 ml) and anisole (0.34 ml) for 20 minutes in an ice bath. The product is purified by recrystallisation from ethyl acetate. Melting point: 200°–203° C (with decomposition). Thin layer chromatogram on silica gel: $Rf_{52A} = 0.26$; $Rf_{67} = 0.25$; $Rf_{101} = 0.52$; $Rf_{101A} = 0.48$; $[\alpha]_D^{20} = -67° \pm 1°$ (c = 0.788 in dimethylsulphoxide).

The starting material can be prepared as follows:

Using the process of Example 1, 7β-[D(−)-α-(2,6-dioxo- 1,2,3,6-tetrahydro-4-pyrimidinecarbonyloxy)-phenylacetamido]- 3-[(1-methyl-1H-tetrazol-5-ylthio)-methyl]-ceph-3-em-4- carboxylic acid benzhydryl ester is obtained by reaction of D(−)-α-(2,6-dioxo-1,2,3,6-tetrahydro-4-pyrimidinecarbonyloxy)-phenylacetic acid with 7β-amino-3-[(1-methyl-1H-tetrazol-5- ylthio)-methyl]-ceph-3-em-4-carboxylic acid benzhydryl ester in a 4:1 mixture of tetrahydrofurane and methylene chloride, in the presence of N,N'-dicyclohexyl-carbodiimide. The product is purified by precipitation with ether from ethyl acetate solution. Melting point:

162°–164° C, with decomposition. Thin layer chromatogram on silica gel (running agent: toluene/ethanol (9.5 : 0.5)): Rf =0.13.

EXAMPLE 3

Using the process of Example 1, 7β-[D(—)-α-(2,4-dioxo-1,2,3,4-tetrahydro-5-pyrimidinecarbonyloxy)-phenylacetamido]-cephalosporanic acid is obtained by treating 7β-[D(—)- α-(2,4-dioxo-1,2,3,4-tetrahydro-5-pyrimidinecarbonyloxy)- phenylacetamido]-cephalosporanic acid benzhydryl ester (0.70 g) with trifluoroacetic acid (10 ml) in a mixture of benzene (4.00 ml) and anisole (0.11 ml) for 10 minutes in an ice bath. The product is purified by precipitation with ether from methanol solution. Thin layer chromatogram on silica gel: $Rf_{52A}$ = 0.25, $Rf_{67}$ = 0.15; $Rf_{101}$ = 0.52; $Rf_{101A}$ = 0.43; melting point 188-192° C (decomposition); $[\alpha]_D^{20}$ = +16° ± 1° (c = 0.820, in dimethylsulphoxide).

The starting material can be prepared as follows:

A solution of 10.0 g of D(—)-mandelic acid benzhydryl ester of melting point 92°–94° C, 8.0 g of uracil-5-carboxylic acid and 12.0 g of N,N′-dicyclohexyl-carbodiimide in 35 ml of hexamethylphosphoric acid triamide is stirred at room temperature, with exclusion of moisture. After stirring for 24 hours, a further 3.0 g of N,N′-dicyclohexyl-carbodiimide are added to the suspension and stirring is continued. After a total reaction time of 4 days, 35 ml of ethyl acetate are added to the reaction mixture, the insoluble by-product is filtered off and the filter residue is washed with ethyl acetate. The filtrate is then diluted with a large amount of ethyl acetate and washed five times with water, the organic phase is dried over sodium sulphate and the solvent is evaporated off on a rotary evaporator at 45° C. The oil which remains is mixed with a 1:1 mixture of ethyl acetate and petroleum ether whereupon the product is obtained. After recrystallisation from acetonitrile, D(—)-α-(2,4-dioxo- 1,2,3,4-tetrahydro-5-pyrimidinecarbonyloxy)-phenylacetic acid benzhydryl ester melts, with decomposition, at 223°–225° C. Thin layer chromatogram on silica gel (running agent: chloroform/ethyl acetate/ethanol (9.5:9.5:1.0)): Rf = 0.20.

A suspension of 1.10 g of D(—)-α-(2,4-dioxo-1,2,3,4-tetrahydro-5-pyrimidinecarbonyloxy)-phenylacetic acid benzhydryl ester in a mixture of 5.0 ml of benzene and 0.26 g of anisole is cooled to +5° C, 10 ml of trifluoroacetic acid are added and the whole is stirred for 15 minutes in an ice bath, with exclusion of atmospheric moisture, whereby a clear solution is obtained. The product is then precipitated from the reaction mixture by adding 100 ml of ether and is filtered off, washed with ether and recrystallised from a little methanol and ethyl acetate. D(—)-α-(2,4-Dioxo-1,2,3,4- tetrahydro-5-pyrimidinecarbonyloxy)-phenylacetic acid melts, with decomposition, at 210°–212° C. Thin layer chromatogram on silica gel: $Rf_{52A}$ = 0.47; $[\alpha]_D^{20}$ = −52° ± 1° (c = 1.144, in dimethylsulphoxide).

Using the process of Example 1, 7β-[D(—)-α-(2,4-dioxo-1,2,3,4-tetrahydro-5-pyrimidinecarbonyloxy)-phenylacetamido]-cephalosporanic acid benzhydryl ester is obtained by reaction of D(—)-α-(2,4-dioxo-1,2,3,4-tetrahydro-5-pyrimidinecarbonyloxy)-phenylacetic acid (1.00 g) with 7β-amino-cephalosporanic acid benzhydryl ester (1.49 g) in tetrahydrofurane (30 ml) in the presence of N,N′-dicyclohexylcarbodiimide (0.70 g or 0.70 g). The product is purified by chromatography on a 30-fold amount of silica gel. Eluant: methylene chloride/methyl acetate (1:1). Thin layer chromatogram on silica gel (running agent: toluene/ethanol (9:1)) Rf: 0.22.

EXAMPLE 4

Using the process of Example 1, 7β-[D(—)-α-(1,6-dihydro-6-oxo-3-pyridazinecarbonyloxy)-phenylacetamido]- cephalosporanic acid is obtained by treating 7β-[D(—)-α- (1,6-dihydro-6-oxo-3-pyridazinecarbonyloxy)-phenylacetamido]- cephalosporanic acid benzhydryl ester (3.2 g) with trifluoroacetic acid (60 ml) in a mixture of benzene (15 ml), methylene chloride (15 ml) and anisole (0.49 ml) for 10 minutes in an ice bath. The product is purified by recrystallisation from ethyl acetate. Melting point: 203°–206° C (with decomposition). Thin layer chraomtogram on silica gel: $Rf_{52A}$ = 0.30; $Rf_{67}$ = 0.25; $Rf_{101}$ = 0.55; $Rf_{101A}$ = 0.45. $[\alpha]_D^{20}$ = +23° ± 1° (c = 1.050, in dimethylsulphoxide).

The starting material can be prepared as follows:

A solution of 13.0 g of 1,6-dihydro-6-oxo-3-pyridazinecarboxylic acid chloride in 120 ml of N,N-dimethylformamide is added dropwise over the course of 1 hour to a solution of 24.0 g of D(—)-mandelic acid benzhydryl ester in 120 ml of pyridine whilst stirring and cooling with an ice bath; the ice bath is then removed and the reaction mixture is stirred overnight at room temperature. The suspension is then poured into a large amount of water and is extracted three times with a 1:1 mixture of benzene and ethyl acetate. The organic phases are combined, washed successively with a large amount of water, 2N hydrochloric acid, water, 1N sodium bicarbonate and water and dried over sodium sulphate, and the solvent is evaporated off on a rotary evaporator at 45° C. D(—)-α-(1,6-Dihydro-6-oxo-3-pyridazinecarbonyloxy)-phenylacetic acid benzhydryl ester is recrystallised from a mixture of benzene and petroleum ether. Melting point: 153°–157° C (with decomposition). Thin layer chromatogram on silica gel (running agent: toluene/ethanol (9.5 : 0.5)): Rf = 0.28. $[\alpha]_D^{20}$ = −48° ±1° (c = 4.170 in chloroform).

A solution of 3.67 g of D(—)-α-(1,6-dihydro-6-oxo-3-pyridazinecarbonyloxy)-phenylacetic acid benzhydryl ester in a mixture of benzene (10 ml), methylene chloride (10 ml) and anisole (0.77 ml) is cooled to +5° C, 45 ml of trifluoroacetic acid are then added and the mixture is stirred for 10 minutes in an ice bath with exclusion of atmospheric moisture. 80 ml of toluene are then added to the reaction mixture, the whole is concentrated greatly on a rotary evaporator at 45° C and D(—)-α-(1,6-dihydro-6-oxo-3-pyridazinecarbonyloxy)-phenylacetic acid is precipitated by adding a mixture of ethyl acetate, ether and petroleum ether. Melting point: 80°–85° C (with decomposition). Thin layer chromatogram on silica gel: $Rf_{52A}$ = 0.45. $[\alpha]_D^{20}$ = −110° ± 1° (c = 1.251, in dimethylsulphoxide).

Using the process of Example 1, 7β-[D(—)-α-(1,6-dihydro-6-oxo-3-pyridazine carbonyloxy)-phenylacetamido ]-cephalosporanic acid benzhydryl ester is obtained by reaction of D(—)-α-(1,6-dihydro-6-oxo-3-pyridazinecarbonyloxy)-phenylacetic acid with 7β-aminocephalosporanic acid benzhydryl ester in tetrahydrofurane in the presence of N,N′-dicyclohexylcarbodiimide. The product is purified by chromatography on silica gel. Thin layer chromatogram on silica gel (running agent: toluene/ethanol (9:1)): RF = 0.41.

EXAMPLE 5

Using the process of Example 1, 7β-[D(—)-α-(1,6-dihydro-6-oxo-3-pyridazinecarbonyloxy)-phenylacetamido]-3- [(1-methyl-1H-tetrazol-5-yl)-thiomethyl]-ceph-3-em-4-carboxylic acid is obtained by treating 7β-[D(—)-α-(1,6-dihydro-6-oxo-3-pyridazinecarbonyloxy)-phenylacetamido]-3-[(1-methyl-1H-tetrazol-5-yl)-thiomethyl]-ceph-3-em-4-carboxylic acid benzhydryl ester (5.1 g) with trifluoroacetic acid (50 ml) in a mixture of benzene (10 ml), methylene chloride (10 ml) and anisole (0.56 ml) for 10 minutes in an ice bath. The product is purified by precipitation with ether from ethyl acetate solution. Melting point: 176°–178° C (with decomposition). Thin layer chromatogram on silica gel: $Rf_{52A} = 0.25$; $Rf_{67} = 0.20$; $Rf_{101} = 0.54$; $Rf_{101A} = 0.46$. $[\alpha]_D^{20} = -55° \pm 1°$ (c = 1.220 in dimethylsulphoxide).

The starting material can be prepared as follows:

Using the process of Example 1, 7β-[D(—) -α-(1,6-dihydro-6-oxo-3-pyridazinecarbonyloxy)-phenylacetamido]-3-[(1-methyl-1H-tetrazol-5-yl)-thiomethyl]-ceph-3-em-4-carboxylic acid benzhydryl ester is obtained by reaction of D(—)-α-(1,6-dihydro-6-oxo-3-pyridazinecarbonyloxy)-phenylacetic acid (prepared as in Example 4) with 7β-amino-3-[(1-methyl-1H-tetrazol-5-ylthio)-methyl]-ceph-3-em-4-carboxylic acid benzhydryl ester in a 2:1 mixture of tetrahydrofurane and methylene chloride in the presence of N,N'-dicyclohexylcarbodiimide. The product is purified by chromatography on silica gel. Thin layer chromatogram on silica gel (running agent: toluene/ethanol, 85 : 15): Rf = 0.42.

EXAMPLE 6

Using the process of Example 1, 7β-[D(—)-α-(2-hydroxy-5-pyridinecarbonyloxy)-phenylacetamido]-cephalosporanic acid is obtained by treating 7β-[D(—)-α-(2-hydroxy-5-pyridine-carbonyloxy)-phenylacetamido]-cephalosporanic acid benzhydryl ester (3.4 g) with trifluoroacetic acid (40 ml) in a mixture of benzene (15 ml), methylene chloride (10 ml) and anisole (0.54 ml) for 10 minutes in an ice bath. The product is purified by recrystallisation from a mixture of methanol and ethyl acetate. Melting point: 230°–232° C (with decomposition). Thin layer chromatogram on silica gel: $Rf_{52A} = 0.30$; $Rf_{67} = 0.32$; $Rf_{101} = 0.55$; $Rf_{101A} = 0.49$. $[\alpha]_D^{20} = +14° \pm 1°$ (c = 1.007 in dimethylsulphoxide).

The starting material can be prepared as follows:

Using the process of Example 4, D(—)-α-(2-hydroxy-5-pyridinecarbonyloxy)-phenylacetic acid benzhydryl ester is obtained by reaction of D(—)-mandelic acid benzhydryl ester (11.0 g) with 2-hydroxy-5-pyridinecarboxylic acid chloride (6.8 g) in a mixture of pyridine (40 ml), N,N-dimethylformamide (25 ml) and methyl chloride (15 ml). The product is purified by recrystallisation from a mixture of benzene and petroleum ether. Melting point: 156°–160° C (with decomposition). Thin layer chromatogram on silica gel (running agent: toluene/ethanol (9.5 : 0.5)): Rf = 0.19. $[\alpha]_D^{20} = -43° \pm 1°$ (c = 4.411, in chloroform).

Using the process of Example 4, D(—)-α-(2-hydroxy-5-pyridinecarbonyloxy)-phenylacetic acid is obtained by treating D(—)-α-)2-hydroxy-5-pyridinecarbonyloxy)-phenylacetic acid benzhydryl ester (5.5 g) with trifluoroacetic acid (40 ml) in a mixture of benzene (20 ml) and anisole (1.35 ml) for 10 minutes in an ice bath. The product is purified by recrystallisation from ethyl acetate. Melting point: 208°–210° C (with decomposition). Thin layer chromatogram on silica gel: $Rf_{52A} = 0.60$. $[\alpha]_D^{20} = -120° \pm 1°$ (c = 1.292 in dimethylsulphoxide).

Using the process of Example 1, 7β-[D(—)-α-(2-hydroxy-5-pyridinecarbonyloxy)-phenylacetamido]-cephalosporanic acid benzhydryl ester is obtained by reaction of D(—)-α-(2-hydroxy-5-pyridinecarbonyloxy)-phenylacetic acid with 7β-amino-cephalosporanic acid benzhydryl ester in a 6 : 1 mixture of tetrahydrofurane and dioxane in the presence of N,N'-dicyclohexylcarbodiimide. The product is purified by chromatography on silica gel. Thin layer chromatogram on silica gel (running agent: toluene/ethanol (9:1)): Rf = 0.35.

EXAMPLE 7

Using the process of Example 1, 7β-[D(—)-α-(2-hydroxy-4-quinolinecarbonyloxy)-phenylacetamido]-cephalosporanic acid is obtained by treating 7β-[D(—)-α-(2-hydroxy-4-quinolinecarbonyloxy)-phenylacetamido]-cephalosporanic acid benzhydryl ester (3.0 g) with trifluoroacetic acid (40 ml) in a mixture of benzene (20 ml), methylene chloride (10 ml) and anisole (0.45 ml) for 10 minutes in an ice bath. The product is purified by recrystallisation from ethyl acetate. Melting point: 175°–178° C (with decomposition). Thin layer chromatogram on silica gel: $Rf_{52A} = 0.45$; $Rf_{67} = 0.30$; $Rf_{101} = 0.54$; $Rf_{101A} = 0.48$. $[\alpha]_D^{20} = +37° \pm 1°$ (c = 1.137 in dimethysulphoxide).

The starting material can be prepared as follows:

Using the process of Example 4, D(—)-α-(2-hydroxy-4-quinolinecarbonyloxy)-phenylacetic acid benzhydryl ester is obtained by reaction of D(—)-mandelic acid benzhydryl ester (12.0 g) with 2-hydroxy-4-quinolinecarboxylic acid chloride (6.6 g) in a mixture of pyridine (60 ml), N,N-dimethylformamide (30 ml) and hexamethylphosphoric acid triamide (30 ml). The product is purified by recrystallisation from a mixture of benzene and petroleum ether. Melting point: 202°–20° C (with decomposition). Thin layer chromatogram on silica gel (running agent: toluene/ethanol (9.5 : 0.5)): Rf = 0.26. $[\alpha]_D^{20} = 41° \pm 1°$ (c = 4.043, in chloroform).

Using the process of Example 4, D(—)-α-(2-hydroxy-4-quinolinecarbonyloxy)-phenylacetic acid is obtained by treating D(—)-α-(2hydroxy-4-quinolinecarbonyloxy)-phenylacetic acid benzhydryl ester (9.0 g) with trifluoroacetic acid (60 ml) in a mixture of benzene (30 ml) and anisole (2.0 ml) for 10 minutes in an ice bath. The product is purified by recrystallisation from methanol. Melting point: 122°–124° C (with decomposition). Thin layer chromatogram on silica gel: $Rf_{52A} = 0.50$. $[\alpha]_D^{20} = 47° \pm 1°$ (c = 1.186 in dimethylsulphoxide).

Using the process of Example 1, 7β-[D(—)-α-(2-hydroxy-4-quinolinecarbonyloxy)-phenylacetamido]-cephalosporanic acid benzhydryl ester is obtained by reaction of D(—)-α-(2-hydroxy-4-quinolinecarbonyloxy)-phenylacetic acid with 7β-amino-cephalosporanic acid benzhydryl ester in tetrahydrofurane in the presence of N,N'-dicyclohexylcarbodiimide. The product is purified by recrystallisation from ethyl acetate. Melting point: 158°–160° C (with decomposition). Thin layer chromatogram on silica gel (running agent: toluene/ethanol (9:1)): Rf = 0.32.

EXAMPLE 8

Using the process of Example 1, 7β-[D(—)-α-(3,5-dioxo-2,3,4,5-tetrahydro-1,2,4-triazine-6-carbonyloxy)- phenylacetamido]-cephalosporanic acid is obtained by treating 7β-[D(—)-α-(3,5-dioxo-2,3,4,5-tetrahydro-1,2,4-triazine-6-carbonyloxy)-phenylacetamido]-cephalosporanic acid benzhydryl ester (5.0 g) with trifluoroacetic acid (40 ml) in a mixture of benzene (20 ml) and anisole (0.76 ml) for 10 minutes in an ice bath. The product is purified by recrystallisation from ethyl acetate. Melting point: 158°–160° C (with decomposition). Thin layer chromatogram on silica gel: $Rf_{52A} = 0.31$; $Rf_{67} = 0.25$; $Rf_{101} = 0.56$; $Rf_{101A} = 0.47$. $[α]_D^{20} = +23° ± 1°$ (c = 0.942, in dimethylsulphoxide).

The starting material can be prepared as follows:

Using the process of Example 4, D(—)-α-(3,5-dioxo-2,3,4,5-tetrahydro-1,2,4-triazine-6-carbonyloxy)-phenylacetic acid benzhydryl ester is obtained by reaction of D(—)-mandelic acid benzhydryl ester (10.0 g) with 3,5-dioxo-2,3,4,5-tetrahydro-1,2,4-triazine-6-carboxylic acid chloride (5.6 g) in a mixture of pyridine (25 ml), N,N-dimethylformamide (25 ml) and tetrahydrofurane (35 ml). The product is purified by recrystallisation from ethyl acetate/petroleum ether. Melting point: 197°–200° C (with decomposition). $[α]_D^{20} = -59° ± 1°$ (c = 2.872, in dimethylsulphoxide).

Using the process of Example 4, D(—)-α-(3,5-dioxo-2,3,4,5-tetrahydro-1,2,4-triazine-6-carbonyloxy)-phenylacetic acid is obtained by treating D(—)-α-(3,5-dioxo-2,3,4,5-tetrahydro-1,2,4-triazine-6-carbonyloxy)-phenylacetic acid benzhydryl ester (6.3 g) with trifluoroacetic acid (60 ml) in a mixture of benzene (30 ml) and anisole (1.5 ml) for 10 minutes in an ice bath. The product is purified by recrystallisation from ethyl acetate. Melting point: 216°–217° C (with decomposition). Thin layer chromatogram on silica gel: $Rf_{52A} = 0.47$. $[α]_D^{20} = -101° ± 1°$ (c = 0.963 in dimethylsulphoxide).

Using the process of Example 1, 7β-[D(—)-α-(3,5-dioxo-2,3,4,5-tetrahydro-1,2,4-triazine-6-carbonyloxy)-phenylacetamido]-cephalosporanic acid benzhydryl ester is obtained by reaction of D(—)-α-(3,5-dioxo-2,3,4,5-tetrahydro-1,2,4-triazine-6-carbonyloxy)-phenylacetic acid with 7β-aminocephalosporanic acid benzhydryl ester in tetrahydrofurane in the presence of N,N'-dicyclohexylcarbodiimide. The product is purified by chromatography on silica gel. Thin layer chromatogram on silica gel (running agent: toluene/ethanol (9:1)): Rf = 0.25.

EXAMPLE 9

Preparation of the sodium salt of 7β-[D(—)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid:

A solution of 3.0 g of 7β-[D(—)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid in 50 ml of methanol is taken, 2.6 ml of a 2 molar solution of sodium 2-ethyl-hexanoate in methanol are added whilst stirring and cooling in an ice bath, and thereafter the reaction mixture is left to stand for 30 minutes at room temperature. 300 ml of diethyl ether are then added dropwise to the clear solution, whilst stirring, whereupon the sodium salt precipitates. It is filtered off, washed with diethyl ether and dried in a high vacuum at room temperature.

EXAMPLE 10

Dry powders or phials, containing 0.6 g of the sodium salt of 7β-[D(—)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid, are prepared as follows:

Composition (for 1 ampoule or phial):

Sodium salt of 7β-[D(—)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid — 0.6 g Mannitol — 0.06 g A sterile aqueous solution of the sodium salt of 7β-[D(—)-α-(2,6-dioxo-1,2,3,6-tetrahydro-4-pyrimidinecarbonyloxy)-phenylacetamido]-3-](1-methyl-1H-tetrazol-5-ylthio)-methyl]-ceph-3-em-4-carboxylic acid and of the mannitol is subjected to freeze-drying in 5 ml ampoules or 5 ml phials under aseptic conditions and the ampoules and phials are sealed and tested.

We claim:

1. A compound of the formula

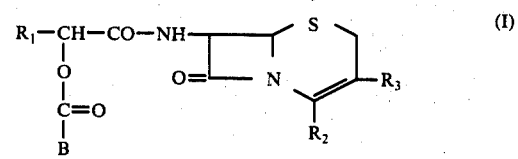

wherein $R_1$ denotes phenyl, thienyl, furyl, 1,4-cyclohexadienyl, or phenyl substituted by methyl, lower alkoxy, hydroxy, halogen or nitro, $R_2$ represents a free carboxyl group or a pivaloyloxymethoxycarbonyl group, $R_3$ represents a heterocyclylthiomethyl group wherein the heterocyclyl radical is 1-oxidized pyridyl, pyrimidyl, pyridazinyl, pyrazinyl, imidazolyl, imidazolidyl, purinyl, triazolyl, tetrazolyl or such radicals substituted by lower alkyl, lower alkoxy, hydroxy or halogen, and B represents the formula ($B_1$)

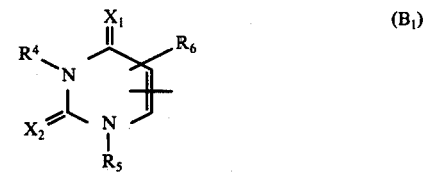

wherein $X_1$ and $X_2$ independently of one another denote oxygen, sulphur or the imino group =NH, $R_4$ and $R_5$ independently of one another denote hydrogen or methyl, and $R_6$ denotes hydrogen, halogen, methyl or phenyl, or represents the formula ($B_2$)

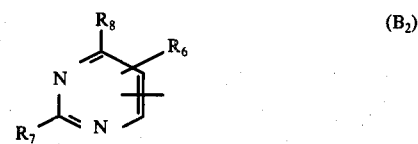

wherein $R_6$ denotes hydrogen, halogen, methyl or phenyl, and $R_7$ and $R_8$ independently of one another denote a free hydroxyl or mercapto group, lower alkoxy, lower alkyl mercapto, lower alkanoyloxy or lower alkanoyl mercapto, halogen or a mono- or di-lower alkylated or lower alkanoylated amino group, and one of the radicals $R_7$ or $R_8$ can also be hydrogen, or represents the formula ($B_5$)

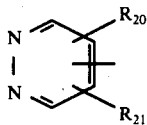

(B₅)

wherein $R_{20}$ denotes a free hydroxyl or mercapto group, lower alkoxy, lower alkyl mercapto, lower alkanoyloxy or lower alkanoyl mercapto, and $R_{21}$ denotes hydrogen, hydroxyl, halogen or methyl, or represents the formula (B₆)

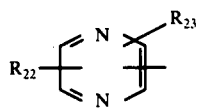

(B₆)

wherein $R_{22}$ denotes a free hydroxyl or mercapto group, lower alkoxy, lower alkyl mercapto, lower alkanoyloxy, or lower alkanoyl mercapto, and $R_{23}$ denotes hydrogen, hydroxyl, halogen or methyl, or represents, where appropriate, a formula tautomeric thereto, or a pharmaceutically acceptable salt thereof.

2. A compound of the formula I according to claim 1, wherein $R_1$ represents phenyl, $R_2$ denotes a carboxyl group, $R_3$ denotes 1-methyl-1H-tetrazol-5-ylthiomethyl, and the group B denotes one of the groups $B_1$, $B_2$, $B_5$ and $B_6$ which is monoasubstituted or disubstituted exclusively be mercapto, hydroxyl or oxo, and wherein the hydroxyl or mercapto groups may also be present in the form of their esters with a mono-lower alkyl carbonic acid or in the free form, or a pharmaceutically acceptable salt thereof.

3. A compound of the formula I according to claim 1, wherein $R_1$ represents phenyl, $R_2$ denotes a carboxyl group, $R_3$ denotes 1-methyl-1H-tetrazol-5-ylthiomethyl and the group B denotes the 2,4-dioxo-1,2,3,4-tetrahydropyrimid-5-yl or the 2,6-dioxo-1,2,3,6-tetrahydropyrimid-4-yl radical, the 1,6-dihydro-6-oxo-3-pyridazinyl, or a pharmaceutically acceptable salt thereof.

4. A compound according to claim 1 which is 7β-[D(−)-α-(2,6-dioxo-1,2,3,6-tetrahydro-4-pyrimidinecarbonyloxy)-phenylacetamido]-3-[(1-methyl-1H-tetrazol-5-ylthio)-methyl]-ceph-3-em-4-carboxylic acid or a pharmaceutically acceptable salt thereof.

5. A compound according to claim 1 which is 7β-(D(−)-α-(1,6-dihydro-6-oxo-3-pyridazinecarbonyloxy)-phenylacetamido]-3-[(1-methyl-1H-tetrazol-5-yl)-thiomethyl]-ceph-3-em-4-carboxylic acid or a pharmaceutically acceptable salt thereof.

6. An antibacterial composition comprising an antibacterially effective amount of a compound of claim 1 together with a pharmaceutically usable excipient.

7. A method for the treatment of infections caused by microorganisms which comprises administering to a host suffering such infection an antibacterially effective amount of a compound of claim 1.

* * * * *